(12) United States Patent
Mostowfi et al.

(10) Patent No.: US 10,379,100 B2
(45) Date of Patent: Aug. 13, 2019

(54) METHOD OF PREDICTING THE CONCENTRATION OF ASPHALTENES USING A FIRST PRECIPITANT AND CORRELATION BACK TO AN ASPHALTENE CONCENTRATION MEASUREMENT USING A SECOND PRECIPITANT

(71) Applicant: SCHLUMBERGER TECHNOLOGY COPORATION, Sugar Land, TX (US)

(72) Inventors: Farshid Mostowfi, Lexington, MA (US); Vincent Joseph Sieben, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/564,802

(22) PCT Filed: Apr. 7, 2015

(86) PCT No.: PCT/US2015/024615
§ 371 (c)(1),
(2) Date: Oct. 6, 2017

(87) PCT Pub. No.: WO2016/163990
PCT Pub. Date: Oct. 13, 2016

(65) Prior Publication Data
US 2018/0113108 A1 Apr. 26, 2018

(51) Int. Cl.
*G01N 21/75* (2006.01)
*G01N 33/28* (2006.01)
(Continued)

(52) U.S. Cl.
CPC ......... *G01N 33/2823* (2013.01); *E21B 49/08* (2013.01); *E21B 49/10* (2013.01);
(Continued)

(58) Field of Classification Search
CPC .......... G01N 33/2823; G01N 33/2835; G01N 21/05; G01N 21/82; G01N 21/31;
(Continued)

(56) References Cited

U.S. PATENT DOCUMENTS

| 8,269,961 B2 | 9/2012 | Mostowfi et al. |
| 9,278,351 B2 | 3/2016 | Mostowfi et al. |

(Continued)

FOREIGN PATENT DOCUMENTS

WO    2015023343 A1    2/2015

*Primary Examiner* — Michael P Stafira (57) ABSTRACT

A method for determining the asphaltene content of oil includes obtaining an oil sample, determining an optical spectrum of the oil sample and removing asphaltenes from the oil sample by precipitating asphaltenes using a first alkane precipitant. The method also includes determining an optical spectrum of maltenes of the oil sample and subtracting the optical spectrum of the maltenes of the oil sample from the optical spectrum of the oil sample to yield an optical spectrum of asphaltenes of the oil sample. The method further includes using the optical spectrum of asphaltenes of the oil sample to determine asphaltene content of the oil sample using a second alkane precipitant.

20 Claims, 9 Drawing Sheets

(51) Int. Cl.
*E21B 49/10* (2006.01)
*E21B 49/08* (2006.01)
*G01N 21/05* (2006.01)
*G01N 21/31* (2006.01)
*G01N 21/84* (2006.01)
*G01N 31/02* (2006.01)

(52) U.S. Cl.
CPC ............ *G01N 21/05* (2013.01); *G01N 21/314* (2013.01); *G01N 21/75* (2013.01); *G01N 21/84* (2013.01); *G01N 31/02* (2013.01); *G01N 33/2835* (2013.01); *E21B 2049/085* (2013.01); *G01N 2021/8472* (2013.01)

(58) Field of Classification Search
CPC ........ G01N 21/59; G01N 21/83; G01N 31/16; G01N 33/42; G01N 21/85; G01N 21/79; G01N 24/081; G01N 31/162; G01N 2001/4061; G01N 2021/8472; G01N 21/314; G01N 21/3577; G01N 21/75; G01N 21/84; G01N 30/02; G01N 31/02; G01N 1/28; G01N 1/4055; G01N 2001/381; G01N 21/00; G01N 21/25; G01N 21/80; G01N 21/954; G01N 2201/12; G01N 22/00; G01N 30/95; G01N 33/24; G01N 33/28; G01N 33/2805; G01N 33/287; G01N 1/12; G01N 1/38; G01N 1/4077; G01N 2001/4083; G01N 2001/4088; G01N 2021/258; G01N 2030/027; G01N 2030/062; G01N 21/27; G01N 21/3504; G01N 21/359; G01N 21/534; G01N 21/553; G01N 2201/129; G01N 24/10; G01N 25/14; G01N 30/06; G01N 30/90; G01N 30/96; G01N 33/0031

See application file for complete search history.

(56) References Cited

U.S. PATENT DOCUMENTS

| | | | |
|---|---|---|---|
| 9,346,049 B2 | 5/2016 | Mostowfi et al. | |
| 2004/0058451 A1 | 3/2004 | Pauli et al. | |
| 2011/0292382 A1 | 12/2011 | Mostowfi et al. | |
| 2013/0071934 A1* | 3/2013 | Indo | G01N 21/80 436/28 |
| 2014/0369889 A1* | 12/2014 | Mostowfi | G01N 33/2823 422/82.09 |
| 2014/0375991 A1 | 12/2014 | Schneider et al. | |
| 2015/0176407 A1* | 6/2015 | Indo | G01N 21/31 702/6 |

\* cited by examiner

METHOD OF PREDICTING THE CONCENTRATION OF ASPHALTENES USING A FIRST PRECIPITANT AND CORRELATION BACK TO AN ASPHALTENE CONCENTRATION MEASUREMENT USING A SECOND PRECIPITANT

BACKGROUND

Field

The present application relates to methods of predicting the concentration of asphaltenes in a sample of oil, such as crude oil.

Description of Related Art

Petroleum composition data plays a role in guiding both upstream and downstream operations, including: predicting fluid behavior inside a petroleum reservoir, providing flow assurance during transportation of the petroleum, understanding potential outcomes when mixing, blending, or diluting the petroleum, and directing refinement processes. Separating the crude oil into its constituent parts or "fractions" is a fundamental operation when characterizing the composition of the crude oil.

Briefly, crude oils can be separated into two fractions: asphaltenes and maltenes. The maltene fraction includes saturate, aromatic, and resin molecules. Once separated, the fractions can be quantified and analyzed. The asphaltenes are normally dissolved in the crude oil, but can be precipitated out of solution by titrating the crude oil with an alkane precipitant, such as heptane. Thereafter, the precipitated asphaltenes can be filtered from the resulting crude oil mixture, which constitutes the maltenes.

Figure 1A:
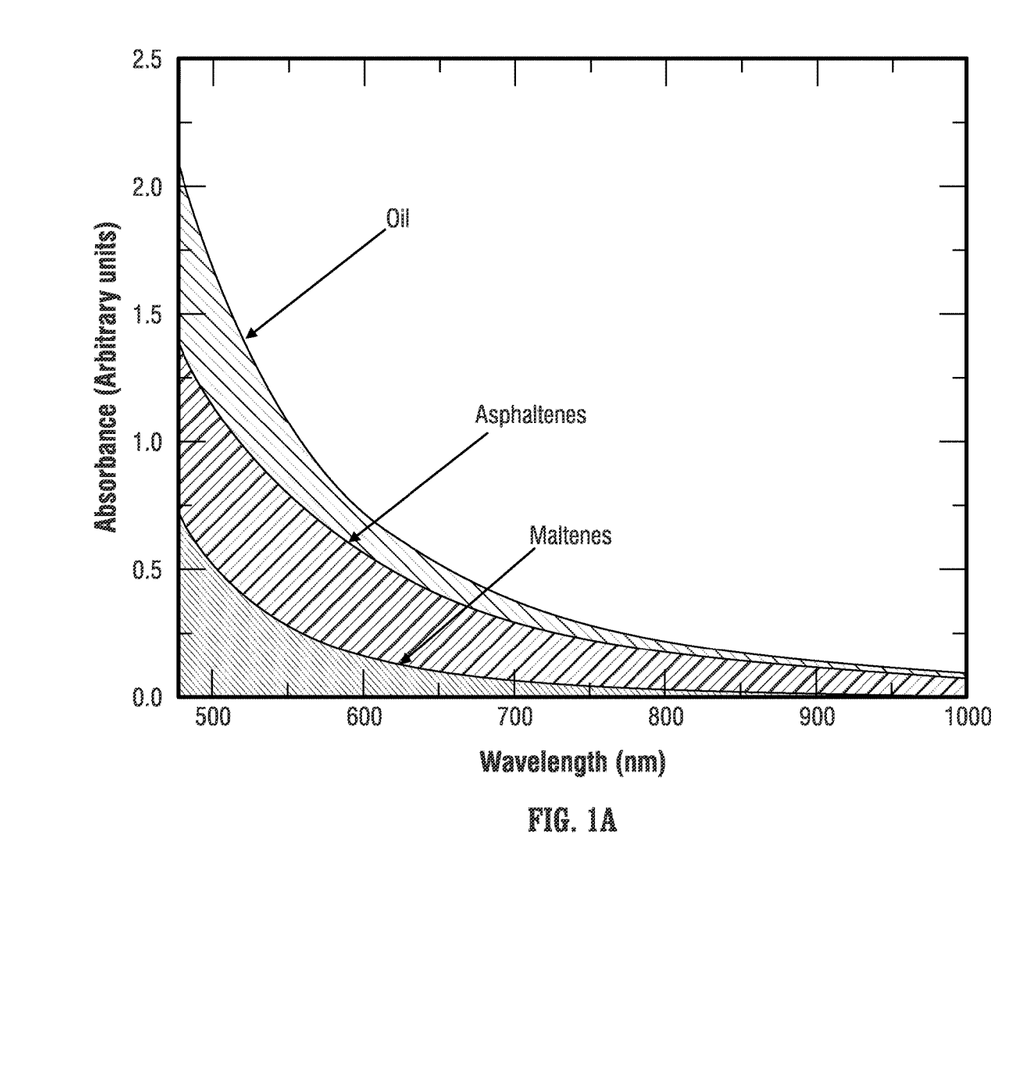
FIG. 1A is a graphical representation of the optical spectra of an oil sample and its constituent maltenes and asphaltenes.

U.S. Pat. No. 8,269,961 (hereinafter "Mostowfi '961") and International Patent Application Publication WO 2013/126732 (hereinafter "Mostowfi '732") describe how the optical spectrum of the crude oil and the optical spectrum of the maltenes can be used to determine the content of asphaltenes in the crude oil. Specifically, Mostowfi '961 and Mostowfi '732 note that the optical spectrum of crude oil is the sum of the optical spectra of its constituent fractions, the asphaltenes and the maltenes. FIG. 1A shows typical optical spectra of oil, asphaltenes, and maltenes in the visible range. The optical spectrum of the maltenes can be obtained after the asphaltenes are separated and the optical spectrum of the crude oil can be obtained before the asphaltenes are precipitated from the crude oil. The optical spectrum of asphaltenes can be obtained by subtracting the optical spectrum of maltenes from the optical spectrum of the crude oil.

In both Mostowfi '961 and Mostowfi '732 the determination of asphaltene concentration is based on the difference between the optical absorbance of crude oil before and after precipitation of asphaltenes. Specifically, the difference in absorbance between the crude oil with dissolved asphaltenes and the crude oil sample without the precipitated asphaltenes (after titration with heptane), is correlated to the weight concentration of asphaltenes and such correlations correlate well to conventional wet chemistry techniques such as those described in ASTM D6560, which are based on titration of crude oil using a heptane precipitant. Thus, the optical data is based on titration of the crude oil sample with the same precipitant as used in the wet chemistry techniques used to correlate the data. As a result, a direct correlation between the optical data and the wet chemistry data is possible.

However, the maximum temperature at which the asphaltene precipitant is effective in precipitating the asphaltenes is limited by the boiling point of the precipitant (e.g., 98.42° C. for heptane at atmospheric pressure). For example, rather than precipitating asphaltenes from the crude oil, at temperatures above 98.42° C. heptane would vaporize at atmospheric pressure making optical absorbance measurements of the crude oil and maltenes difficult. Thus, at elevated temperatures above the boiling point of heptane, it would be technologically challenging to use the technique described in Mostowfi '961 and Mostowfi '732 based on heptane as the precipitant to correlate optical data with wet chemistry data according to ASTM D6560.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method is described for predicting the concentration of asphaltenes at elevated temperature conditions. In one embodiment, the techniques described in Mostowfi '961 and Mostowfi '732 are adapted by using a precipitant having a boiling point that is above the temperature of the oil sample into which it is titrated. However, using a precipitant that differs from what is specified in ASTM D6560 results in a different partition of asphaltenes and maltenes from the oil, such that optical data obtained from the techniques described in Mostowfi '961 and Mostowfi '732 are not directly correlatable to wet chemistry data obtained using ASTM D6560. The method described herein includes a correlation of obtained absorbance data of an oil sample with asphaltenes precipitated by a high boiling point precipitant to a standard wet chemistry measurement of asphaltenes precipitated at ambient conditions using another precipitant, such as heptane in accordance with ASTM D6560. Correlation back to the standard wet chemistry measurement at ambient conditions according to ASTM D6560 is helpful because it is a commonly accepted and performed testing technique.

Also, another method is described for predicting the concentration of asphaltenes by obtaining absorbance data from an oil sample precipitated using a first alkane precipitant (e.g., dodecane) and correlating the obtained absorbance data to other absorbance data corresponding to another oil sample precipitated using a second alkane precipitant, such as decane. Where the absorbance data corresponding to the second alkane precipitant is itself correlated to asphaltene concentration data, the correlation between the two sets of absorbance data can be used to correlate the absorbance data corresponding to the first alkane precipitant to the asphaltene concentration.

Illustrative embodiments of the present disclosure are directed to a method and apparatus for determining the asphaltene fraction of an oil sample. The method (and corresponding apparatus) involves a sequence of operations including: obtaining an oil sample; determining an optical spectrum of the oil sample; removing asphaltenes from the oil sample by precipitating asphaltenes with a first alkane precipitant; determining an optical spectrum of maltenes of the oil sample precipitated with the first alkane precipitant; subtracting the optical spectrum of the maltenes of the oil sample from the optical spectrum of the oil sample to yield an optical spectrum of asphaltenes of the oil sample; and using the optical spectrum of the asphaltenes of the oil sample to determine the asphaltene content of the oil sample using a second alkane precipitant.

The first alkane precipitant may be an alkane having an order higher than that of heptane, such as octane, nonane, decane, undecane, dodecane, tridecane, tetradecane, pentadecane, or hexadecane.

The second alkane precipitant may be an alkane having an order lower than that of the first precipitant, such as heptane, hexane, or pentane.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment numerous implementation-specific decisions can be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As used herein, the term "microfluidics" or "microfluidic" refers to a device, apparatus or system that deals with the behavior, precise control, and manipulation of fluids that are geometrically constrained to a small, commonly sub-millimeter, scale. The device, apparatus, or system can employ small, commonly sub-millimeter, scale channels that are etched into planar substrates, such as glass, where networks of these embedded channels transport the sample from one operation to the next. The manipulation of small volumes of fluid enables precise control of reagents and seamless automation of several consecutive operations.

The present disclosure relates to a system and method for determining the asphaltene content of an oil. Generally, oil is made up of asphaltenes and maltenes. Separation of asphaltenes requires addition of an alkane, such as heptane (C7), at, for example, a 1:40 volume ratio, although higher volume ratios or volume ratios as low as 1:1 or less are also satisfactory. Once the precipitant (C7) is added, the asphaltenes aggregate and precipitate out of the solution. The asphaltenes can then be separated using a membrane filtration unit. The maltenes fraction permeates through the filter and the optical spectrum of maltenes may be measured downstream of the filter using a spectrometer.

The optical spectrum of the oil before asphaltene precipitation can be measured and compared to the optical spectrum of the maltenes after precipitation. In the case of the microfluidic system disclosed in Mostowfi '732, a sample of the oil before asphaltene precipitation is optionally diluted with toluene at 1:80 volume ratio to reduce the darkness of the sample before measurement of its optical spectrum. As noted in Mostowfi '961 and Mostowfi '732, the difference between the optical spectrum of the oil before asphaltene precipitation and the optical spectrum of the maltenes after asphaltene precipitation can be correlated to the mass concentration of the asphaltenes precipitated, e.g., with heptane (C7), using conventional wet chemistry techniques such as ASTM D6560. However, while the techniques described in Mostowfi '961 and Mostowfi '732 work well under laboratory conditions using heptane (C7) as the precipitant, heptane and toluene have temperature limitations (high vapor pressure curves) that do not readily permit their use with those techniques when performed under elevated temperature conditions, and more specifically, at high temperature conditions, such as those that may occur downhole, where the presence of bubbles caused by solvent or precipitant vaporization will make optical absorbance measurements difficult.

To adapt the techniques described in Mostowfi '961 and Mostowfi '732 for elevated temperature conditions, precipitants (alkanes of higher order than that of heptane) that have boiling points that are higher than heptane (C7) may be substituted for heptane. The higher boiling point precipitants may have boiling points that are higher than 200° C., such as dodecane ($C_{12}H_{26}$) or tetradecane ($CH_3(CH_2)_{12}CH_3$). However, using a precipitant other than heptane results in a different partitioning of the asphaltenes and maltenes from the oil sample, such that the absorbance data obtained for asphaltenes precipitated with the higher order alkane precipitant (i.e., the difference between the optical spectrum of the oil and the optical spectrum of the maltenes after the asphaltenes are precipitated with the higher boiling point precipitant) may not be directly correlated to the mass concentration of asphaltenes precipitated with heptane (C7) at ambient conditions using conventional wet chemistry (e.g., gravimetric) techniques such as ASTM D6560.

To adjust for the differences in the different partitioning of the oil fractions resulting from the use of higher order precipitants, the absorbance data of the asphaltenes precipitated with the higher order precipitant can be determined based on asphaltene content data obtained from oil samples precipitated with heptane at ambient conditions using standard wet chemistry techniques.

As will be described below, it has been found that there is a correlation between the absorbance of the asphaltenes precipitated using higher boiling point, higher order alkanes (e.g., higher order than heptane (C7), such as C10, C12, and C14) and the content of asphaltenes determined at ambient conditions using conventional wet chemistry techniques using heptane (C7), such as ASTM D6560. Therefore, the content of asphaltenes in an oil sample under elevated temperature conditions can be determined based, in part, on (1) the optical spectrum of the asphaltenes obtained by precipitation with a first alkane precipitant (e.g., higher order alkane) and (2) wet chemistry techniques in a lab using a second alkane precipitant (e.g., lower order alkane such as heptane) for the same oil under consideration.

Moreover, as will be described in further detail below, it has been found that absorbance data of asphaltenes precipitated from an oil sample using the above-mentioned first (e.g., higher order) alkane precipitant can be correlated with absorbance data of asphaltenes precipitated from the oil sample using a third alkane precipitant (e.g., another higher order alkane different from the first alkane precipitant). Therefore, after the asphaltene content of oil precipitated with the above-mentioned first precipitant has been determined, as discussed above, (i.e., as a function of the first precipitant used to obtain the absorbance data and the measured absorbance of the asphaltenes), the asphaltene content of the same oil precipitated using a third alkane precipitant (e.g., C12) can also be determined by correlating the absorbance data of asphaltenes precipitated using the third precipitant to the absorbance data of asphaltenes precipitated using the first precipitant.

It will be appreciated that the foregoing discussion may be clarified by referring to the following details related to the concepts discussed above.

Figure 1B:
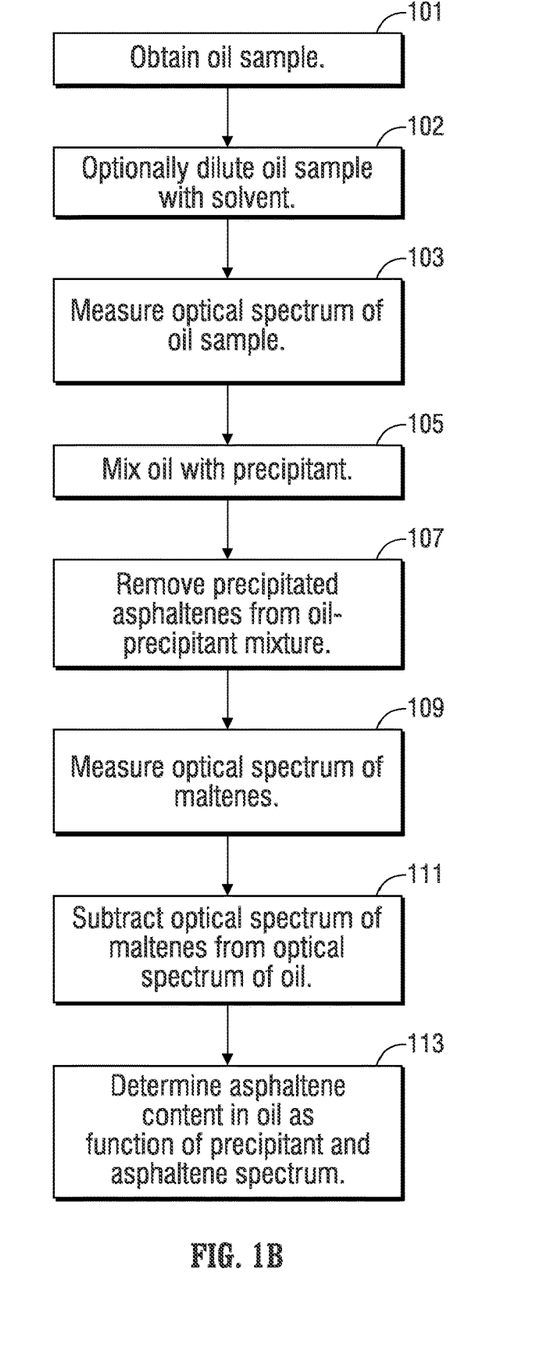
FIG. 1B is a flow chart representing an illustrative embodiment of a method for determining the asphaltene content of oil.

FIG. 1B provides a flow chart representing an illustrative embodiment of a method for determining the asphaltene content of an oil at elevated temperature conditions. In the illustrated embodiment, an oil sample is obtained (block 101). It should be noted that the obtained sample may be a sample that is retrieved and transported to another location, such as a laboratory, for analysis, or a sample that is retrieved and analyzed in the field, as is discussed in greater detail herein. The system and method of the present invention are also capable of being installed and used in a downhole tool. The scope of the present invention is not limited by the means by which the oil sample is obtained.

The optical spectrum of the oil sample, which may be diluted with a solvent such as toluene, xylene, or 1-methylnaphthalene at block 102, is measured at block 103. An undiluted portion of the oil sample is then mixed with a first precipitant at block 105 to precipitate the asphaltenes from the oil. In one embodiment, the first precipitant is an alkane of higher order than heptane (C7), such as tetradecane (C14). The precipitant may be mixed at a ratio of one part oil to 40 parts tetradecane or other suitable ratio. However, other precipitants, such as decane, dodecane or the like, and other mixing ratios are contemplated by the present disclosure.

After the precipitant mixes with the oil, the asphaltenes will precipitate out of solution so that the precipitated asphaltenes may be filtered in order to remove the precipitated asphaltenes from the oil-precipitant mixture (block 107). The portion of the oil remaining after the precipitated asphaltenes are removed comprises maltenes, which are species having lower molecular weights than asphaltenes and are soluble in the first precipitant. The optical spectrum of the maltenes is measured (block 109), which is then subtracted from the optical spectrum of the oil prior to the asphaltenes being removed (block 111). The resulting optical spectrum is the optical spectrum of the asphaltenes in the original oil sample. A predicted value of the weight percentage of asphaltenes in the oil can be determined as a function of the first precipitant and the asphaltene optical spectrum (block 113).

Figure 2:
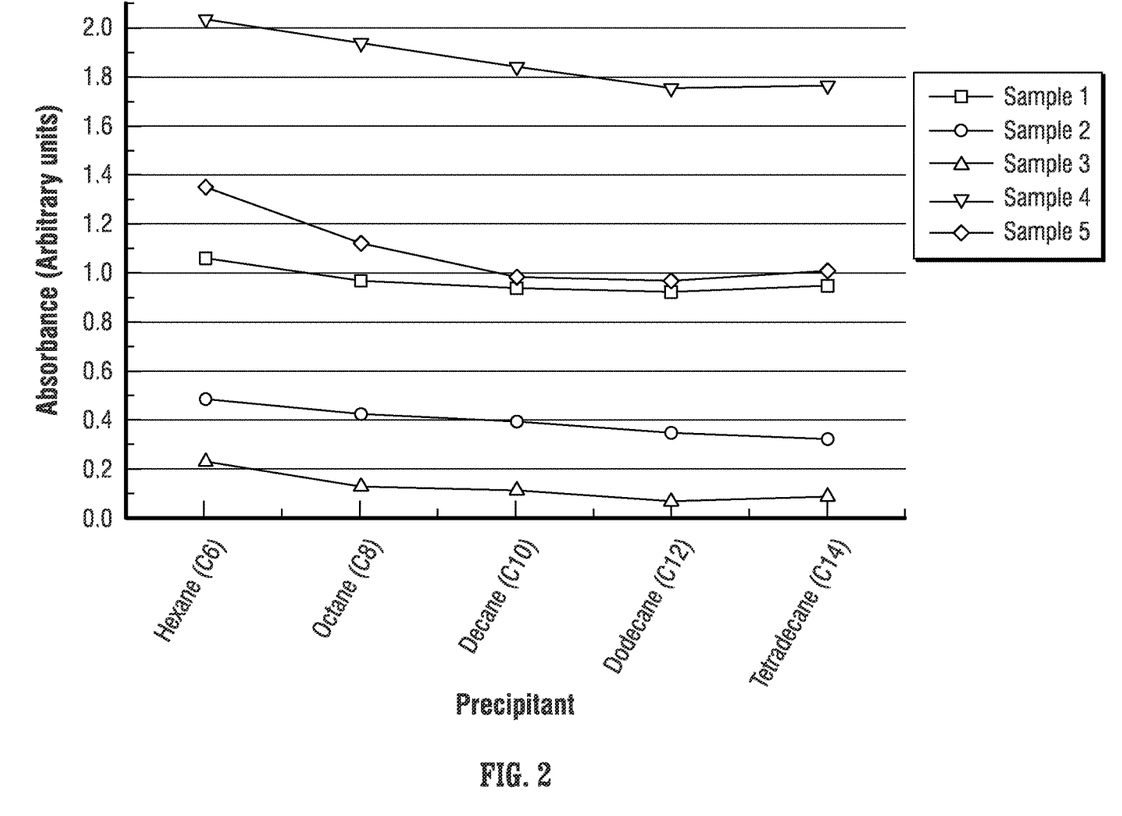
FIG. 2 is a graphical representation of optical absorbance of various samples of crude oil titrated with various alkane precipitants in which the optical spectra of the maltenes of the sample have been subtracted from the optical spectra of the crude oil samples.

FIG. 2 shows asphaltene absorbance as a function of the precipitant for five different crude oil samples. Each sample has a different content of asphaltenes. It is known that higher absorbance corresponds to higher content of precipitated asphaltenes. Thus, as shown in FIG. 2, for each of the five samples, the absorbance (and the amount of precipitated asphaltenes), decreases as the carbon chain length increases (i.e., as the order of alkanes increases, e.g., from hexane (C6) to tetradecane (C14)).

Also notable from the plot in FIG. 2 is that the change in absorbance is proportional to concentration. For example, for crude oil samples having higher asphaltene content (i.e., higher absorbance), such as samples 4 and 5, there is a greater change in absorbance from one precipitant to another as compared to samples having lower asphaltene content, such as samples 2 and 3. Nevertheless, even for both crude oil samples having high and low asphaltene concentrations, as noted above, the absorbance (the amount of precipitated asphaltenes) reaches a relative plateau for carbon chains longer than decane (C10), indicating that such higher order alkane precipitants may be used for precipitation of asphaltenes.

Figure 3A:
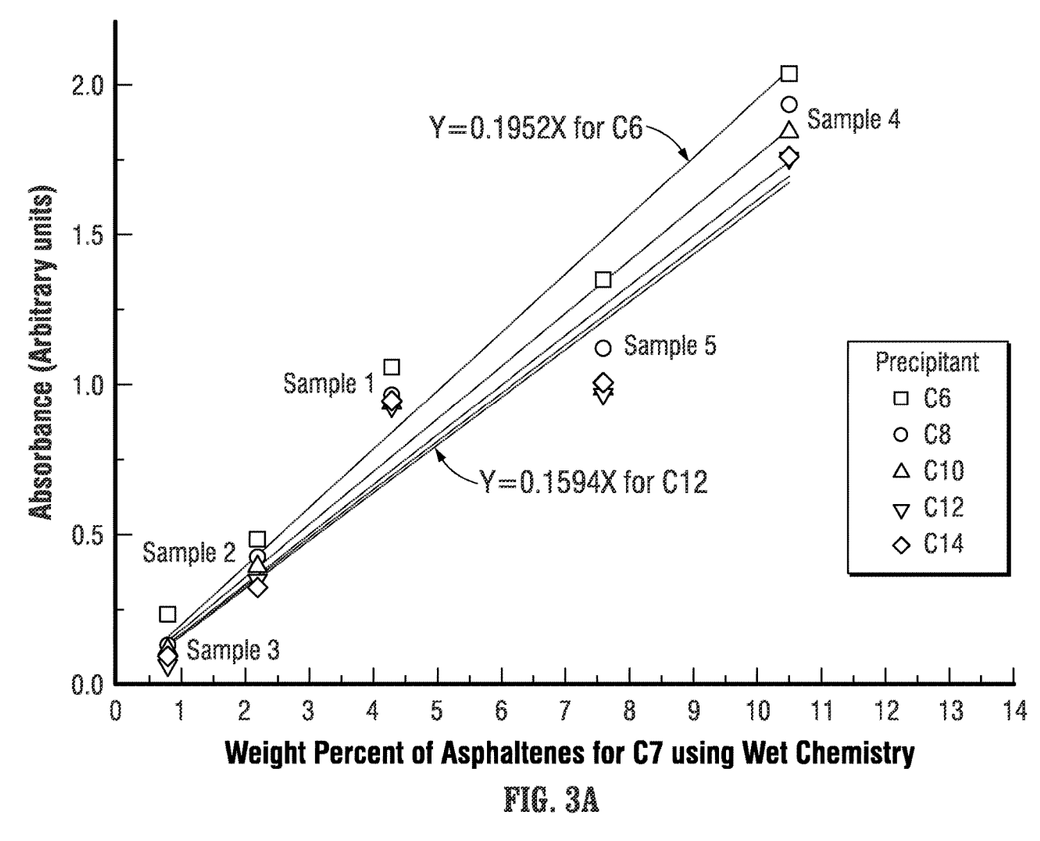
FIG. 3A is a graphical representation of the absorbance data from FIG. 2 plotted against asphaltene weight percentage determined from wet chemistry testing performed for each crude oil sample. Correlation functions are also illustrated in FIG. 3A indicating that absorbance is a function of weight percentage and precipitant used.

FIG. 3A shows a correlation between absorbance of the asphaltenes for different alkane precipitants ranging in order from C6 (hexane) to C14 (tetradecane) versus the weight percent of asphaltenes precipitated using C7 (heptane). The horizontal axis shows the weight percentage of asphaltenes in each of the five crude oil samples precipitated using heptane (C7) at ambient conditions utilizing standard wet chemistry (e.g., gravimetric analysis) techniques in a lab. The vertical axis shows the absorbance data from FIG. 2 plotted for each of the five crude oil samples and for each precipitant noted in FIG. 2.

The plot in FIG. 3A indicates that the absorbance of precipitated asphaltenes precipitated using, say tetradecane (C14), can be correlated to the content of asphaltenes precipitated using heptane (C7) using standard wet chemistry techniques. Specifically, FIG. 3A shows that the content of asphaltenes in a crude oil sample can be represented as a linear function of the absorbance of the asphaltenes and the precipitant used to obtain the asphaltene optical spectrum. For example, the line shown plotted for dodecane (C12) as the precipitant may be used to correlate absorbance data for another oil sample back to the mass of asphaltenes obtained using heptane (C7) precipitated using wet chemistry techniques. This finding is notable because it may be used to predict the weight percentage of asphaltenes in oil samples precipitated using a first precipitant, for example of higher order than heptane (and also higher boiling point than heptane), by correlating the respective absorbance data of the asphaltenes back to mass percentage data of the oil sample precipitated using a second precipitant, for example of lower order than the first precipitant (e.g., heptane).

Figure 3B:
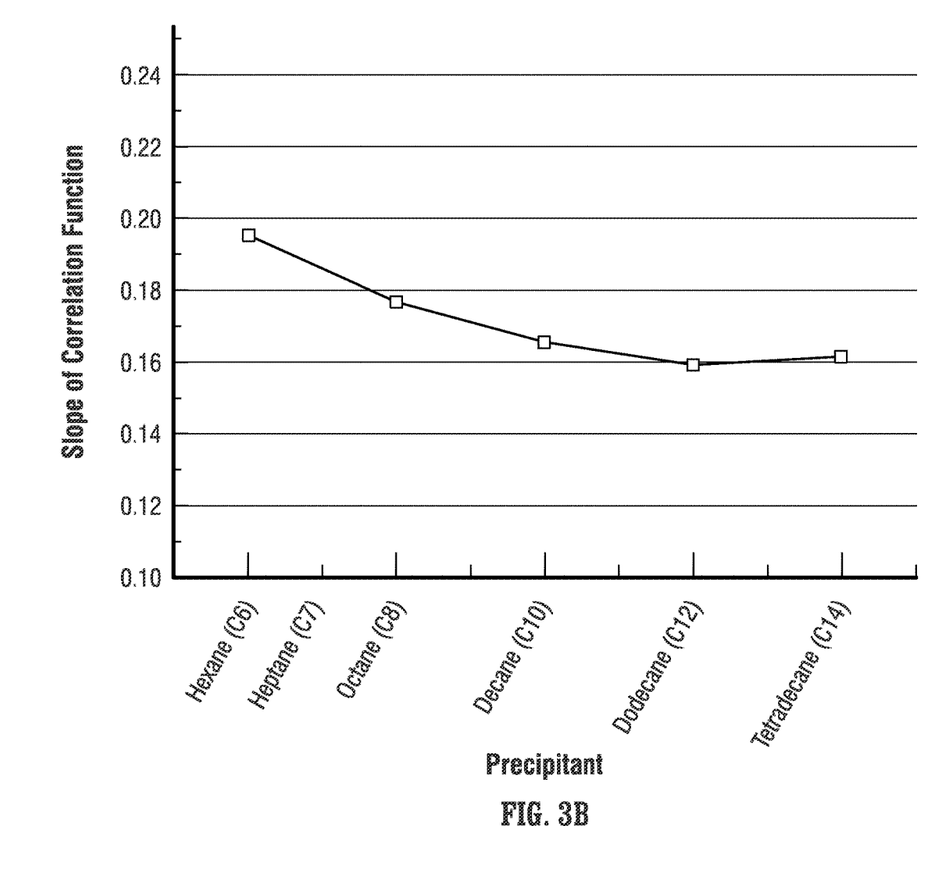
FIG. 3B is a plot of the slope of the correlation functions plotted in FIG. 3A for each of the precipitants.

The plot in FIG. 3B also indicates that the slopes of the correlation lines change from a maximum of 0.1952 for hexane (C6) as the precipitant to a minimum of 0.1594 for dodecane (C12) as the precipitant. Also, the difference between the slopes for using dodecane (C12) and tetradecane (C14) as precipitants is considered to be within the resolution of the method, further indicating that use of higher order alkanes beyond decane (C10), does not appreciably alter the results of the analysis of the asphaltene concentration.

Moreover, it has been found that the absorbance of asphaltenes precipitated using different alkane precipitants correlate to each other as a function of molecular size of the precipitant. Therefore, by measuring the absorbance of asphaltenes using a first precipitant, the absorbance of asphaltenes precipitated using a second precipitant can be estimated using a linear correlation.

Figure 4A:
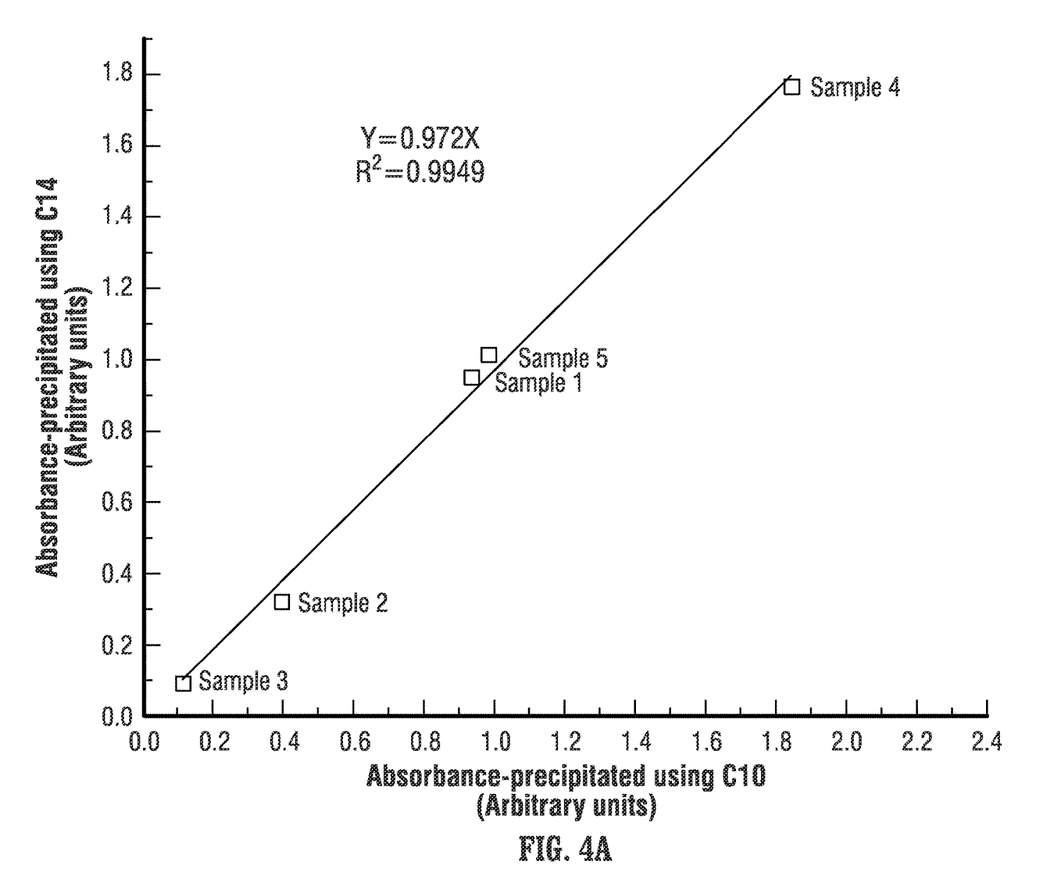
FIG. 4A is a graphical representation of the correlation between the optical absorbance of asphaltenes precipitated using decane and tetradecane.
Figure 4B:
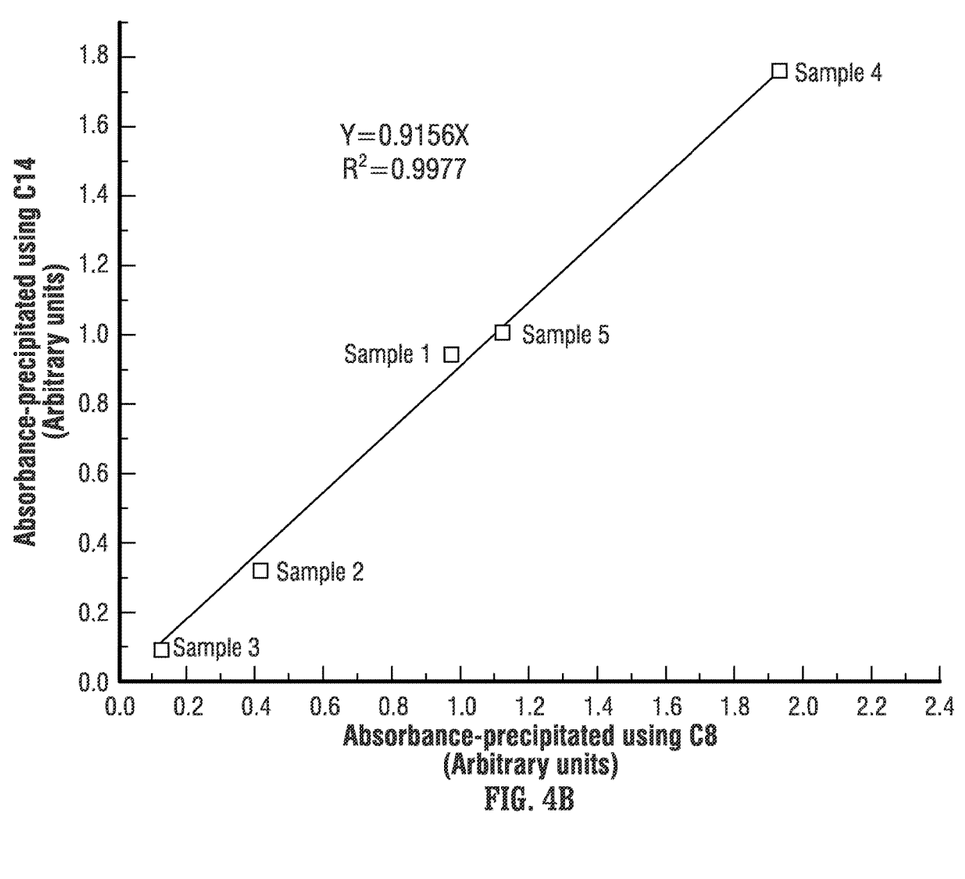
FIG. 4B is a graphical representation of the correlation between the optical absorbance of asphaltenes precipitated using octane and tetradecane.

FIG. 4A shows the absorbance measurements of asphaltenes precipitated using decane (C10) and tetradecane (C14). The linear correlation shows a fit with an R-squared of 0.9949, which indicates that the absorbances of asphaltenes precipitated using at least those two different alkanes as precipitants are highly correlated. Also, FIG. 4B shows the absorbance measurements of asphaltenes precipitated using octane (C8) and tetradecane (C14). The linear correlation shows a fit with an R-squared of 0.9977, which indicates that the absorbances of asphaltenes precipitated using at least these two different alkanes as precipitants are highly correlated. Therefore, it is possible to measure the absorbance of asphaltenes that are precipitated using tetradecane (C14) and correlate the absorbance back to asphaltenes that are precipitated using another precipitant, such as decane (C10). Then, if the asphaltene optical spectrum absorbance data obtained from precipitating oil with decane (C10) has already been correlated to the content of asphaltene using wet chemistry techniques, as described above, it is also possible to correlate the absorbance data obtained with tetradecane (C14) to the content of asphaltene. It is also possible to directly correlate the optical absorbance of asphaltenes obtained using C14 to the weight percentage using C7.

Figure 5:
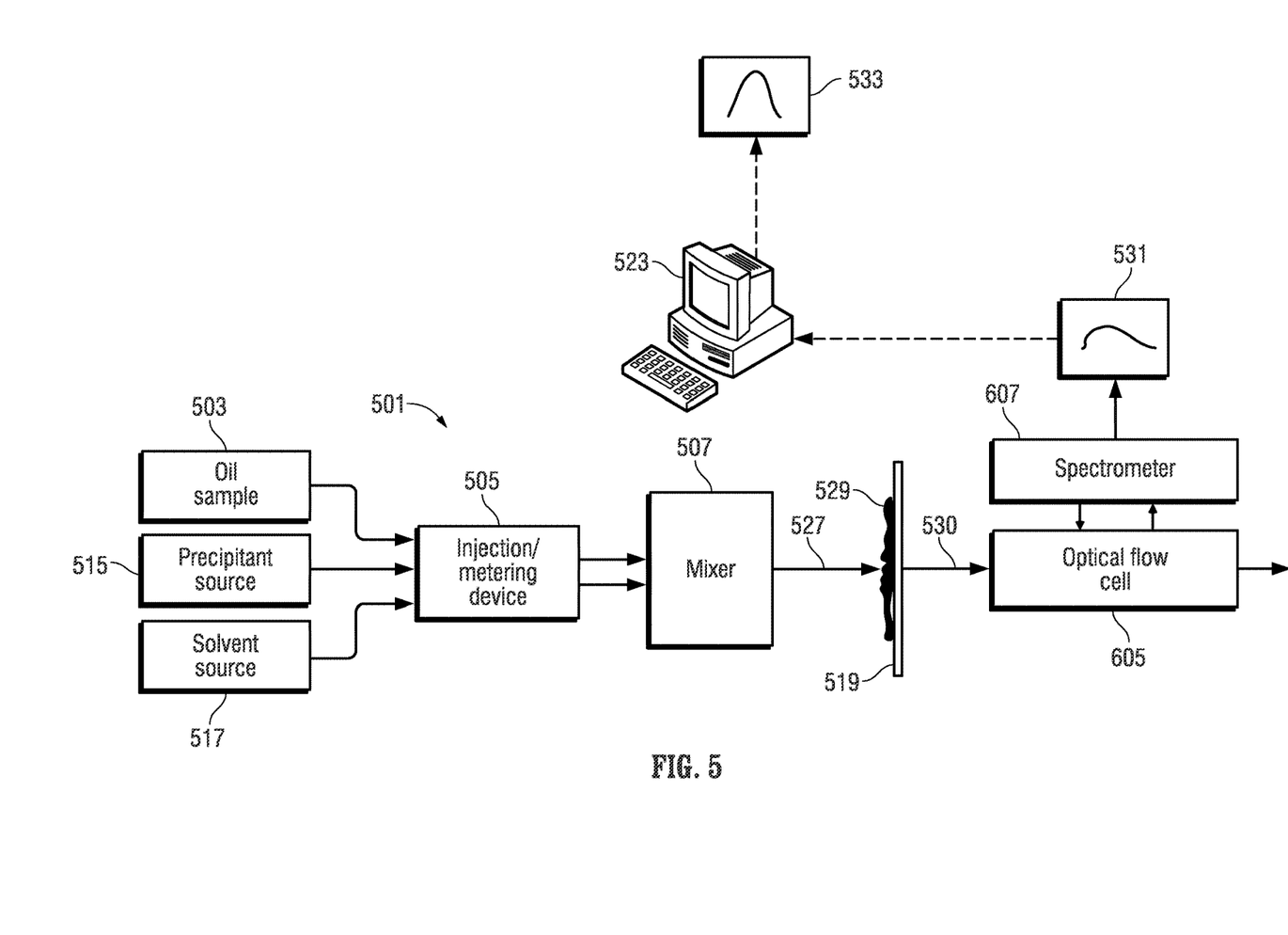
FIG. 5 is a stylized, graphical representation of an illustrative embodiment of a system for determining the asphaltene content of oil.

FIG. 5 depicts an illustrative embodiment of an apparatus 501 for automated fluid analysis of an oil sample using the techniques described with reference to the workflow of FIG. 1B. The apparatus 501 characterizes the asphaltene fraction using spectroscopy. The apparatus includes a reservoir 503 that holds an oil sample. The oil sample can include lighter (more volatile) molecular weight oil components as well as heavy (less volatile) molecular weight components such as heavy oil and bitumen. An injection/metering device 505 can be operated to inject a defined volumetric slug of the oil sample held by the reservoir 503 into a mixer 507.

The apparatus 501 also includes a solvent reservoir 517 from which a solvent such as toluene, xylene, or 1-methyl-naphthalene may optionally be injected to dilute and thereby lighten the oil sample.

Finally, the apparatus 501 includes a reservoir 515 that holds a precipitant that causes asphaltenes to precipitate from an oil sample when present. The precipitant is injected into the mixer 507 using the injection/metering device 505.

The mixer 507 can employ chaotic split and recombine microfluidic mixing techniques or other suitable microfluidic techniques as described in Nguyen and Wu, "Micromixers—a Review," *Journal of Micromechanics and Microengineering* 15, no. 2 (2005): R1, herein incorporated by reference in its entirety.

The injection/metering device 505 can be operated to inject the precipitant alone, the oil alone, or a mixture of a controlled ratio of the precipitant and the oil into the mixer 507. The injection/metering device 505 can be electrically-controlled syringe pumps, such as the Mitos Duo XS-Pump available from The Dolomite Center Limited of Royston, United Kingdom, where the syringe of the respective syringe pumps acts as the reservoirs 503 and 515 that hold an amount of the oil and precipitant, respectively.

When the oil and the precipitant mix in the mixer 507 solid asphaltene content 529 (commonly referred to as asphaltene floccules or asphaltene flock) precipitate from the mixture 527. The asphaltene flock 529 is carried as a suspension in the liquid phase content of the mixture 527. The liquid phase content of the mixture 527 includes maltenes of the oil sample, which are the lower molecular weight components of the oil sample that remain after removing the precipitated asphaltene content. The maltenes are also soluble in the precipitant.

The mixer 507 is fluidly coupled to a filter 519 that provides filtering to trap solid phase hydrocarbon components (i.e., the asphaltene flock 529), while passing soluble liquid phase hydrocarbon components (the permeate 530, which includes the maltenes of the oil sample) to a flow-through optical flow cell 605. The filter 519 may be microfluidic and can also be fluidly coupled to a waste port that allows for flushing and removal of the solid phase hydrocarbon components (i.e., the asphaltene flock 529) that is trapped by the filter 519.

A spectrometer 607 is optically coupled to the flow-through optical flow cell 605 and can be operated to derive an optical spectrum 531 of the fluid that flows from the filter 519 through the optical flow cell 605.

In one embodiment, the optical flow cell 605 can be realized by an optical absorbance flow cell, such as the FIAlab SMA-Z-2.5 cell will fused silica windows and a 2.5 mm optical path and a 2.0 μl internal volume available from FIAlab Instruments, Inc. of Bellevue, Wash., USA. The spectrometer 607 can be realized by a broadband spectrometer, such as the model HR2000+ available from Ocean Optics, Inc. of Dunedin, Fla., USA. The broadband spectrometer can be used in conjunction with a broadband light source which can be based on a tungsten filament bulb (such as the model LS-1 light source available from Ocean Optics, Inc.). Fiber optic waveguides can be used to optically couple the optical flow cell 605 to both a broadband light source and spectrometer 607.

A computer processing system 523 can be programmed with suitable control logic that interfaces to the injection/metering device 505 via wired or wireless signal paths therebetween. The computer processing system 523 can also interface to the spectrometer 607 via wired or wireless signal paths therebetween. The control logic of the computer processing system 523 (which can be embodied in software that is loaded from persistent memory and executed in the computing platform of the computer processing system 523) is configured to control the different parts of the apparatus 501 to carry out an automated sequence of operations (workflow) that characterizes the asphaltene fraction of an oil sample. The control logic can be configured by a testing script, which is input into and executed by the computer processing system 523 to perform automatic control operations as specified by the testing script. The computer processing system 523 can include a graphical user interface 533 that allows the user to specify the sequence of automatic control operations and/or the parameters (such as pressures, flow rates, temperatures, etc.) for such automatic control operations. An example of such an automated workflow is shown in FIG. 1B.

The workflow shown in FIG. 1B can be performed to measure the weight concentration of asphaltenes in a sample of oil.

At block 101, a sample of oil is introduced to the mixer 507, by injection/metering device 505. The oil is then passed through the filter 519 and to the optical flow cell 605.

At block 102 the oil sample may optionally be diluted in mixer 507 with a solvent such as toluene, xylene, or 1-methylnaphthalene before moving to the optical flow cell 605.

At block 103 the spectrometer 607 analyzes the oil in the optical flow cell 605 and determines an optical spectrum of the oil, represented by graph 531. In the illustrated embodiment, the optical spectrum of the oil, i.e., represented by graph 531, is fed to computer processing system 523. The computer processing system 523 is configured to store the optical spectrum as measured in block 103. The computer processing system 523 can determine the average oil absorbance ($Avg_{Oil}$) from the optical spectrum data. Alternatively, the spectrometer 607 can be configured to analyze the oil sample and determine the average oil absorbance, which can then be stored in the computer processing system 523. The flow path of oil in the apparatus 501 is then cleaned.

It is not expected that asphaltenes will be collected by the filter 519 during the operation of block 103. However, in the event that asphaltenes are collected by the filter 519 during the operation of block 103, a cleaning procedure can be executed to remove the collected asphaltenes before continuing to block 105. This cleaning procedure can involve flowing solvent first across the filter 519.

At block 105 samples of oil and dodecane (i.e., a higher order alkane precipitant) are transmitted to the mixer 507 by injection/metering device 505. The flow rates for the oil and the dodecane are configured such that the mixer 507 forms a mixture where the oil sample is diluted with a predetermined concentration of the precipitant. The volume fraction of the precipitant in the mixture can possibly be at or near 40:1 for many oil samples. The sample of oil and the precipitant are mixed in the mixer 507 at a predetermined ratio, such as at a ratio of about one part oil to about 40 parts precipitant.

At block 107, once the sample of oil and the precipitant are mixed, the precipitant causes the asphaltenes in the oil to aggregate and precipitate out in the mixer 507 and the channel 527. The mixer 507 and the channel 527 can allow the precipitant of the sample/precipitant mixture produced by the mixer 507 to precipitate out most if not all of the asphaltene content of the sample/precipitant mixture (if any asphaltene content is present from the oil sample). The resultant sample/precipitant mixture (including the precipitated solid-form asphaltene content) that is produced flows downstream to filter 519, which traps the precipitated solid-form asphaltene content and allows the permeate (i.e., the liquid phase of the sample/precipitant mixture) to pass to the optical flow cell 605.

In block 109, the spectrometer 607 is configured to measure an optical spectrum (represented by graph 531) of the permeate (which includes the maltenes of the oil sample) that flows through the corresponding optical flow cell 605. In this manner, the spectrometer 607 measures an optical spectrum of the maltenes. The computer processing system 523 is further configured to store the optical spectrum of the maltenes as measured in block 109.

At block 109 the computer processing system 523 can determine an average maltenes absorbance ($Avg_{Malt}$) from the optical spectrum data. Alternatively, the spectrometer 607 can be configured to analyze the maltenes and determine the average maltenes absorbance, which can then be stored in the computer processing system 523.

At block 111, the computer processing system 523 processes the optical spectrum measured and stored in block 103 (with the asphaltene content present and dissolved in the oil sample or oil sample/solvent mixture) in conjunction with the optical spectrum measured and stored in block 109 (with the asphaltene content precipitated and removed from the oil sample/precipitant mixture) in order to derive the weight fraction of asphaltene in the oil sample in block 113.

In one example, the processing of block 111 can involve deriving a characteristic optical density or absorbance AU of the asphaltene content of the oil sample by the following equation:

$$AU = (OD@600 \text{ nm}_{Spectrum\ of\ 103} - OD@800 \text{ nm}_{Spectrum\ of\ 103}) - (OD@600 \text{ nm}_{Spectrum\ of\ 109} - OD@800 \text{ nm}_{Spectrum\ of\ 109}). \quad (1)$$

The first term of Eq. (1) is derived from the optical spectrum of block 103 and represents the contribution of both asphaltene content and the maltenes to AU. The second term of Eq. (1) is derived from the optical spectrum of block 109 and represents the contribution of the maltenes alone to AU. The subtraction of the optical density (OD) at 800 nm in both the first and second terms is meant to reduce the error from spectral offset introduced by light scattering and from other errors in the measurements. The characteristic optical density AU of the asphaltene content as derived from Eq. (1) can be used to determine the asphaltene content in the oil sample as a function of the precipitant and the asphaltene optical spectrum, as discussed above.

At block 113 the characteristic optical density AU of the asphaltene content as derived from Eq. (1) is used to determine the asphaltene content in the oil sample as a function of the precipitant and the asphaltene optical spectrum, as discussed above.

Figure 6:
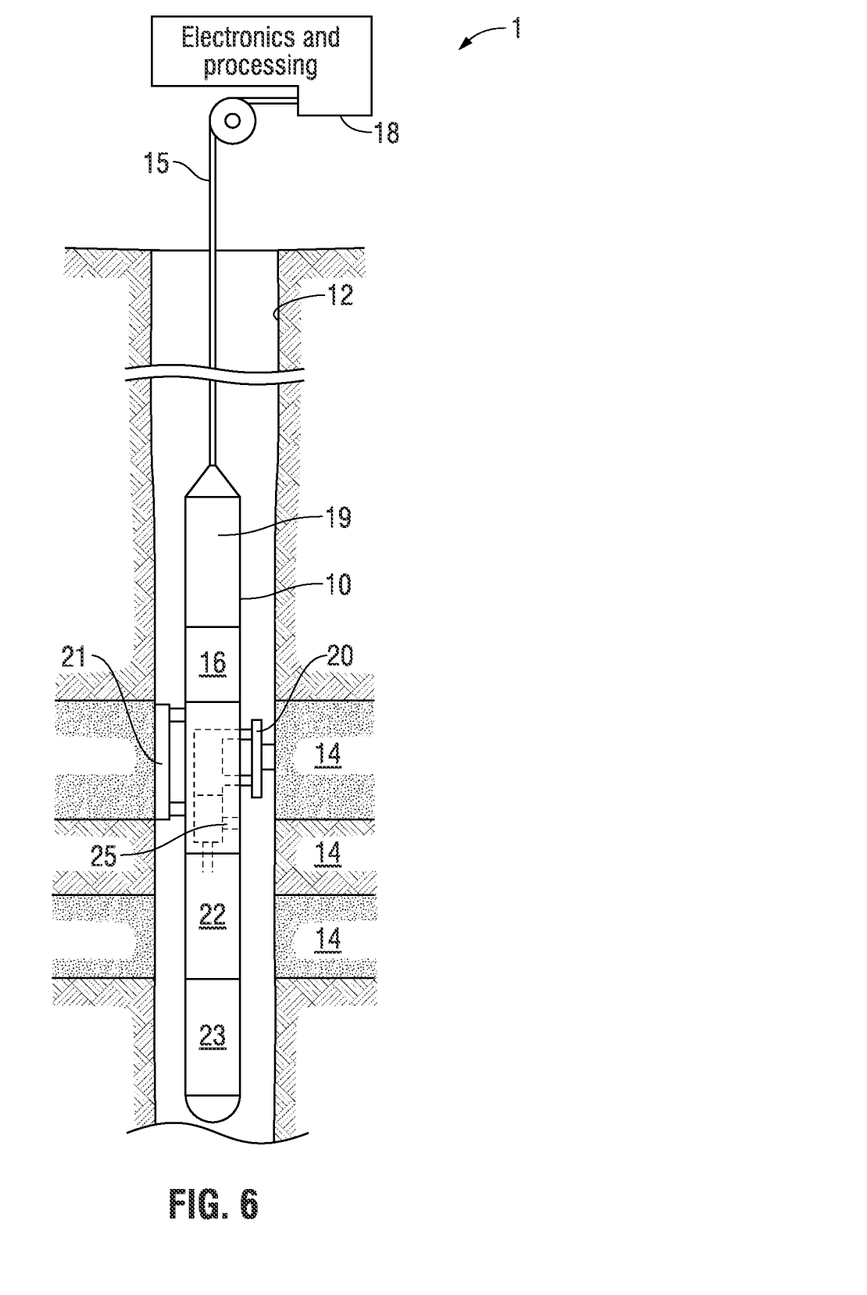
FIG. 6 is a schematic representation of a downhole tool that performs the function of the system of FIG. 5.

FIG. 6 illustrates an exemplary petroleum reservoir analysis system 1 in which the disclosed apparatus may be embodied. The system 1 includes a borehole tool 10 suspended in the borehole 12 from the lower end of a typical multiconductor cable 15 that is spooled in a usual fashion on a suitable winch on the formation surface. The cable 15 is electrically coupled to an electrical control system 18 on the formation surface. The tool 10 includes an elongated body 19, which encloses the downhole portion of the tool control system 16. The elongated body 19 also carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that pressure or fluid communication with the adjacent earth formation 14 is established. Also included with tool 10 are means for determining the downhole pressure and temperature and a fluid analysis module 25 through which the obtained fluid flows. The fluid may thereafter be expelled through a port or it may be sent to one or more fluid collecting chambers 22 and 23, which may receive and retain the fluids obtained from the formation. Control of the fluid admitting assembly 20, the fluid analysis module 25, and the flow path to the collecting chambers 22, 23 is maintained by the tool and electrical control systems 16 and 18. As will be appreciated by those skilled in the art, the surface-located electrical control system 18 includes data processing functionality (e.g., one or more microprocessors, associated memory, and other hardware and/or software) to implement the apparatus as described herein. The electrical control system 18 can also be realized by a distributed data processing system wherein data measured by the tool 10 is communicated (preferably in real-time) over a communication link (typically a satellite link) to a remote location for data analysis as described herein. The data analysis can be carried out on a workstation or other suitable data processing system (such as a computer cluster, computing grid, etc.).

In accordance with the present disclosure the tool 10 of FIG. 6 may function as the apparatus 501 of FIG. 5 and in accordance with the workflow of FIG. 1B to characterize the compositional components of a reservoir of interest and analyze fluid properties of the reservoir of interest based upon its compositional components. For example, one of the fluid collecting chambers 22 and 23 may correspond to the oil sample reservoir 503 and precipitant reservoir 515, respectively, of the apparatus 501 of FIG. 5. Also, the electrical control system 18 may correspond to the computer processing system 523 of the apparatus 501 of FIG. 5. A sample of formation fluid may be obtained at one or more reference stations within the borehole 12 at the reservoir pressure and temperature. The obtained formation fluid samples may be stored in the collecting chambers 22 and 23 and processed by a fluid analysis module 25, which may include the functionality of the injection/metering device 505, mixer 507, filter 519, optical flow cell 605, and spectrometer 607 of the apparatus 501. Thus, in at least one embodiment, the fluid analysis module 25 may measure absorption spectra of oil and deasphaltated oil and translate such measurements into concentrations of asphaltenes in the oil in the formation in accordance with the workflow of FIG. 1B.

The particular embodiments disclosed above are illustrative only, as the disclosed method may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present method is shown in a limited number of forms, it is not limited to just these forms, but is amenable to various changes and modifications.

What is claimed is:

1. A method for characterizing asphaltene content of an oil sample, comprising:
   (a) obtaining the oil sample;
   (b) determining an optical spectrum of the oil sample;
   (c) removing asphaltenes from the oil sample to yield maltenes of the oil sample by precipitating asphaltenes using a first alkane precipitant, wherein the first alkane precipitant has a molecular formula with a number of carbon atoms greater than that of heptane;
   (d) determining an optical spectrum of the maltenes of the oil sample precipitated with the first alkane precipitant in (c);
   (e) determining spectral data related to asphaltenes of the oil sample by subtracting at least part of the optical spectrum of (d) from a corresponding part of the optical spectrum of (b); and
   (f) using a correlation that relates the spectral data as determined in (e) to concentration of asphaltenes in the oil sample as measured by precipitation using a second alkane precipitant, wherein the second alkane precipitant has a molecular formula with a number of carbon atoms equal to or less than heptane.

2. The method of claim 1, wherein the oil sample of (a) is diluted with a solvent before its optical spectrum is determined in (b) and the operations of (c) and (d) are conducted on the oil sample of (a) without diluting the oil sample of (a).

3. The method of claim 2, wherein the solvent is selected from the group consisting of toluene, xylene, or 1 methyl-naphthalene.

4. The method of claim 1, wherein the optical spectrum of the oil sample is determined in (b) by analyzing at least a portion of the oil sample with a spectrometer.

5. The method of claim 1, wherein the asphaltenes are removed from the oil sample in (c) by mixing the oil sample with the first alkane precipitant and removing precipitated asphaltenes from the oil-precipitant mixture.

6. The method of claim 5, wherein the oil sample is mixed with the first alkane precipitant in a microfluidic mixer.

7. The method of claim 5, wherein the precipitated asphaltenes are removed from the oil-precipitant mixture using a microfluidic filter.

8. The method of claim 1, wherein the optical spectrum of (d) is determined by analyzing at least a portion of the maltenes of the oil sample of (c) with a spectrometer.

9. The method of claim 1, wherein the spectral data related to asphaltenes of the oil sample is determined in (e) by i) subtracting a part of the optical spectrum of (d) at a longer wavelength from a part of the optical spectrum of (d) at a shorter wavelength and ii) subtracting a part of the optical spectrum of (b) at the longer wavelength from a part of the optical spectrum of (b) at the shorter wavelength and iii) subtracting the result of (i) from the result of ii).

10. The method of claim 9, wherein the longer wavelength is 800 nanometers and the shorter wavelength is 600 nanometers.

11. The method of claim 1, wherein the first alkane precipitant is selected from the group consisting of octane, nonane, decane, undecane, dodecane, tridecane, tetradecane, pentadecane, and hexadecane.

12. The method of claim 1, wherein the second alkane precipitant is selected from the group consisting of heptane, hexane, and pentane.

13. The method of claim 1, wherein the correlation of (f) is performed on a computer processing system using a correlation function that relates the spectral data as determined in (e) to concentration of asphaltenes in the oil sample as measured by precipitation using the second alkane precipitant.

14. A method for characterizing asphaltene content of an oil sample, comprising:
   (a) obtaining the oil sample;
   (b) determining an optical spectrum of the oil sample;
   (c) removing asphaltenes from the oil sample to yield maltenes of the oil sample by precipitating asphaltenes using a first alkane precipitant, wherein the first alkane precipitant has a molecular formula with a number of carbon atoms greater than that of heptane;
   (d) determining an optical spectrum of the maltenes of the oil sample precipitated with the first alkane precipitant in (c);
   (e) determining spectral data related to asphaltenes of the oil sample by subtracting at least part of the optical spectrum of (d) from a corresponding part of the optical spectrum of (b); and
   (f) using a correlation that relates the spectral data as determined in (e) to concentration of asphaltenes in the oil sample as measured by precipitation using a second alkane precipitant, wherein the second alkane precipitant is different from the first alkane precipitant and has a molecular formula with a number of carbon atoms greater than that of heptane; and
   (g) using a correlation that relates the spectral data as determined in (e) to concentration of asphaltenes in the oil sample as measured by precipitation using a third alkane precipitant, wherein the third alkane precipitant has a molecular formula with a number of carbon atoms equal to or lower than heptane.

15. The method of claim 14, wherein the correlation of (f) is performed on a computer processing system using a first correlation function that relates the spectral data as determined in (e) to concentration of asphaltenes in the oil sample as measured by precipitation using the second alkane precipitant.

16. The method of claim 15, wherein the correlation of (g) is performed on the computer processing system using a second correlation function that relates the spectral data as determined in (e) to concentration of asphaltenes in the oil sample as measured by precipitation using the third alkane precipitant.

17. The method of claim 16, wherein the spectral data related to asphaltenes of the oil sample as determined in (e) comprises a characteristic optical density or absorbance, wherein the first correlation function relates the characteristic optical density or absorbance to concentration of asphaltenes in the oil sample as measured by precipitation using the second alkane precipitant, and wherein the second correlation function relates the characteristic optical density or absorbance to concentration of asphaltenes in the oil sample as measured by precipitation using the third alkane precipitant.

18. The method of claim 14, which is carried out by a borehole tool with the oil sample at downhole pressure and temperature conditions.

19. The method of claim 13, wherein the spectral data related to asphaltenes of the oil sample as determined in (e) comprises a characteristic optical density or absorbance, and wherein the correlation function relates the characteristic optical density or absorbance to concentration of asphaltenes in the oil sample as measured by precipitation using the second alkane precipitant.

20. The method of claim 1, which is carried out by a borehole tool with the oil sample at downhole pressure and temperature conditions.

* * * * *